US00RE44667E

(19) United States
(12) Reissued Patent
Rock

(10) Patent Number: US RE44,667 E
(45) Date of Reissued Patent: *Dec. 24, 2013

(54) IMPEDANCE SPECTROSCOPY SYSTEM AND CATHETER FOR ISCHEMIC MUCOSAL DAMAGE MONITORING IN HOLLOW VISCOUS ORGANS

(75) Inventor: Emilio Sacristan Rock, Tlalpan (MX)

(73) Assignee: Critical Perfusion, Inc., Danville, CA (US)

( * ) Notice: This patent is subject to a terminal disclaimer.

(21) Appl. No.: 11/787,233

(22) Filed: Apr. 12, 2007

Related U.S. Patent Documents

Reissue of:
(64) Patent No.: 6,882,879
Issued: Apr. 19, 2005
Appl. No.: 09/907,781
Filed: Jul. 18, 2001

U.S. Applications:
(60) Provisional application No. 60/219,281, filed on Jul. 19, 2000.

(51) Int. Cl.
*A61H 39/02* (2006.01)

(52) U.S. Cl.
USPC ..... 600/547; 604/508

(58) Field of Classification Search
USPC ..... 600/547, 898, 300, 506, 536; 604/508, 604/500; 324/600, 601, 602, 609, 643, 644
See application file for complete search history.

(56) References Cited

U.S. PATENT DOCUMENTS 2,008,295 A 7/1935 Smith
2,018,080 A 10/1935 Martienssen
2,184,511 A 12/1939 Bagno et al.
2,729,211 A 1/1956 Peter
3,340,867 A 9/1967 Kubicek et al.

(Continued)

FOREIGN PATENT DOCUMENTS

EP 0797950 A1 10/1997
WO WO 82/00581 A1 3/1982

(Continued)

OTHER PUBLICATIONS

Rigaud, et al. Bioelectrical Impedance Techniques in Medicine. Critical Reviews in Biomedial Engineering. CRC Press, Boca Raton, FL, US. 1996:24(4-6):257-336.

(Continued)

*Primary Examiner* — Henry Yuen
*Assistant Examiner* — Thien S Tran
(74) *Attorney, Agent, or Firm* — Triangle Patents, PLLC

(57) ABSTRACT

An impedance spectroscopy system for monitoring ischemic mucosal damage in hollow viscous organs comprises a sensor catheter and an impedance spectrometer for electrically driving the catheter to obtain a complex tissue impedance spectrum. Once the catheter is in place in one of a patient's hollow viscous organs, the impedance spectrometer obtains the complex impedance spectrum by causing two electrodes in the tip of the catheter to inject a current into the mucosal tissue at different frequencies, while two other electrodes measure the resulting voltages. A pattern recognition system is then used to analyze the complex impedance spectrum and to quantify the severity of the mucosal injury. Alternatively, the complex impedance spectrum can be appropriately plotted against the spectrum of normal tissue, allowing for a visual comparison by trained personnel.

22 Claims, 13 Drawing Sheets

(56) References Cited

U.S. PATENT DOCUMENTS

| | | | | | |
|---|---|---|---|---|---|
| 3,480,003 | A | | 11/1969 | Crites | |
| 4,146,254 | A | * | 3/1979 | Turner et al. | 285/105 |
| RE30,101 | E | | 9/1979 | Kubicek et al. | |
| 4,224,949 | A | | 9/1980 | Scott et al. | |
| 4,437,474 | A | | 3/1984 | Peers-Trevarton | |
| 4,476,872 | A | | 10/1984 | Perlin | |
| 4,498,481 | A | | 2/1985 | Lemke | |
| 4,559,951 | A | | 12/1985 | Dahl et al. | |
| 4,602,809 | A | * | 7/1986 | Ross et al. | 285/50 |
| 4,690,152 | A | | 9/1987 | Juncosa | |
| 4,729,385 | A | | 3/1988 | Juncosa et al. | |
| 4,836,214 | A | | 6/1989 | Sramek | |
| 4,852,580 | A | | 8/1989 | Wood | |
| 4,960,133 | A | | 10/1990 | Hewson | |
| 5,069,223 | A | | 12/1991 | McRae | |
| 5,074,827 | A | * | 12/1991 | Bandy, Jr. | 474/157 |
| 5,109,851 | A | | 5/1992 | Jadvar et al. | |
| 5,158,083 | A | | 10/1992 | Rock et al. | |
| 5,280,429 | A | | 1/1994 | Withers | |
| 5,282,840 | A | | 2/1994 | Hudrlik | |
| 5,304,219 | A | | 4/1994 | Chernoff et al. | |
| 5,306,052 | A | * | 4/1994 | MeGushion | 285/328 |
| 5,335,668 | A | | 8/1994 | Nardella | |
| 5,381,790 | A | | 1/1995 | Kanesaka | |
| 5,423,320 | A | | 6/1995 | Salzman et al. | |
| 5,438,985 | A | | 8/1995 | Essen-Moller | |
| 5,454,377 | A | | 10/1995 | Dzwonczyk et al. | |
| 5,456,254 | A | | 10/1995 | Pietroski et al. | |
| 5,477,854 | A | | 12/1995 | Essen-Moller | |
| 5,479,935 | A | | 1/1996 | Essen-Moller | |
| 5,585,402 | A | | 12/1996 | Moncada et al. | |
| 5,633,801 | A | | 5/1997 | Bottman | |
| 5,657,759 | A | | 8/1997 | Essen-Moller | |
| 5,771,894 | A | | 6/1998 | Richard et al. | |
| 5,788,631 | A | | 8/1998 | Fiddian-Green | |
| 5,807,272 | A | | 9/1998 | Kun et al. | |
| 5,810,742 | A | | 9/1998 | Pearlman | |
| 5,833,625 | A | | 11/1998 | Essen-Moller | |
| 5,848,965 | A | | 12/1998 | Essen-Moller | |
| 5,922,701 | A | | 7/1999 | Araneo | |
| 5,981,590 | A | | 11/1999 | Panigrahi et al. | |
| 5,991,650 | A | | 11/1999 | Swanson et al. | |
| 6,010,453 | A | | 1/2000 | Fiddian-Green | |
| 6,017,881 | A | | 1/2000 | Ammons et al. | |
| 6,032,061 | A | * | 2/2000 | Koblish | 600/372 |
| 6,055,452 | A | | 4/2000 | Pearlman | |
| 6,882,879 | B2 | * | 4/2005 | Rock | 600/547 |
| 6,965,795 | B2 | | 11/2005 | Rock | |
| 7,650,183 | B2 | * | 1/2010 | Rock | 600/547 |
| 2002/0013537 | A1 | | 1/2002 | Rock | |
| 2003/0053416 | A1 | | 3/2003 | Ribas-Corbera | |
| 2005/0070769 | A1 | | 3/2005 | Rock | |
| 2006/0015035 | A1 | | 1/2006 | Rock | |

FOREIGN PATENT DOCUMENTS

| | | | |
|---|---|---|---|
| WO | WO 82/00581 | A1 | 4/1982 |
| WO | WO 82/04182 | | 12/1982 |
| WO | WO 82/04182 | A1 | 12/1982 |
| WO | WO 98/48692 | A1 | 11/1998 |

OTHER PUBLICATIONS

Gebhard, et al. Impedance spectroscopy: a method for surveillance of ischemia tolerance of the heart. Thorac Cardiovasc Surg. 1987 Feb;35(1):26-32.

European search report dated Jan. 27, 2009 for Application No. 8169034.9.

European search report dated Mar. 12, 2002 for Application No. 1116731.9.

European search report dated Aug. 21, 2006 for Application No. 6015389.7.

Rigaud B et al., "Bioelectrical Impedance Techniques in Medicine", Critical Reviews in Biomedial Engineering, CRC Press, Boca Raton, FL, US, vol. 24, No. 4-6, 1996, pp. 257-336.

* cited by examiner

IMPEDANCE SPECTROSCOPY SYSTEM AND CATHETER FOR ISCHEMIC MUCOSAL DAMAGE MONITORING IN HOLLOW VISCOUS ORGANS

Matter enclosed in heavy brackets [ ] appears in the original patent but forms no part of this reissue specification; matter printed in italics indicates the additions made by reissue.

*CROSS-REFERENCE TO RELATED APPLICATIONS*

[This application claims the benefit of a Provisional Application, Ser. No. 60/219,281 filed Jul. 19, 2000.] *This application is a reissue application of U.S. Pat. No. 6,882,879, issued on Apr. 19, 2005, and filed on Jul. 18, 2001 as U.S. patent application Ser. No. 09/907,781, which claims the benefit of U.S. Provisional Application No. 60/219,281, filed Jul. 19, 2000, the contents of which are incorporated herein in their entirety by reference.*

FIELD OF THE INVENTION

The present invention relates to systems and internal sensors for monitoring and quantifying ischemic damage in tissues.

BACKGROUND OF THE INVENTION

The gastrointestinal mucosa is at great risk of ischemia in the critically ill, and its disruption has been shown to be the motor of multiple organ failure, a leading cause of death. Knowledge of the level of damage can help guide therapy, reversing moderate damage and/or preventing further complications. For example, as indicated by path A in FIG. 6, the status of a healthy person's mucosa changes little, if at all, over time. Path C shows how the damage level of an ill person's ischemic mucosa greatly increases over the course of several hours if unchecked. However, as shown by path B, further damage can be arrested if the ischemic damage is detected and an appropriate course of treatment is undertaken. Unfortunately, there exists no clinically suitable method to directly monitor ischemic mucosal damage in the gastrointestinal tract of the critically ill patient.

Impedance spectroscopy has been used to detect ischemia (a condition of inadequate blood flow and oxygen delivery to a given tissue) in biological tissues using different instrumental methods. Impedance spectroscopy differs from other impedance measurements (which have long been used for a variety of biomedical applications such as cardiac output estimation, body fat measurement, and plethismography) in that it involves multiple measurements over a range of frequencies that as a whole contain significantly more information of the structural and electrical properties of the sample. For example, U.S. Pat. No. 5,454,377 to Dzwoczyk et al. teaches the assessment of ischemia in the myocardium, U.S. Pat. No. 5,807,272 to Kun et al. teaches the assessment of ischemia in directly accessible tissues (surface or subjacent tissue), and U.S. Pat. No. 6,055,452 to Pearlman shows the general characterization of the status and properties of tissues. However, none of these references show or describe a clinically acceptable method for impedance spectroscopy measurements of the inner wall of hollow viscous organs such as the gastrointestinal mucosa, in vivo or in situ.

On the other hand, several other methods have been devised to detect and/or monitor gastrointestinal ischemia using different measurement technologies. These include tonometry (as shown in U.S. Pat. Nos. 5,788,631 and 6,010,453 to Fiddian-Green), direct in situ measurement using an electrochemical sensor (as shown in U.S. Pat. No. 5,158,083 to Sacristan), and direct in situ measurement using an optochemical sensor (as shown in U.S. Pat. No. 5,423,320 to Salzman et al.) Additionally, U.S. Pat. No. 5,771,894 to Richards et al. shows external, non-invasive measurement using a magnetometer.

Numerous gastrointestinal catheter combinations, using electrodes or other sensors, have been used over the years for various measurements and medical applications. For example, U.S. Pat. No. 5,657,759 to Essen-Moller discloses a gastrointestinal output catheter, U.S. Pat. Nos. 5,848,965 and 5,438,985, both to Essen-Moller, show a gastric pH sensor/catheter combination, and U.S. Pat. No. 5,477,854 to Essen-Moller discloses a helicobater pylori gastric infection sensor. Furthermore, U.S. Pat. No. 5,833,625 to Essen-Moller shows a gastric reflux monitor, U.S. Pat. No. 6,010,453 to Fiddian-Green shows a pressure nasogastric sump and tonometer combination, U.S. Pat. No. 5,158,083 to Sacristan et al. discloses a miniature $pCO_2$ probe and catheter, and U.S. Pat. No. 5,423,320 to Salzman et al. shows an air tonometry sensor and catheter.

Several therapies have been proposed to limit or reverse the gastrointestinal mucosal damage and/or the associated complications in critical patients, including, for example, aggressive hemodynamic resuscitation (as shown in Gutierrez et al.), NO synthase modulators (as shown in U.S. Pat. No. 5,585,402 to Moncada et al.), rBPI protein (as shown in U.S. Pat. No. 6,017,881 to Ammons et al.), oral glutamine (as shown in U.S. Pat. No. 5,981,590 to Panigrahi et al.), and DHEA (as shown in U.S. Pat. No. 5,922,701 to Araneo). All of these can be optimally effective if they are administered within ideal treatment time windows depending on the status of the mucosa.

Accordingly, it is a primary object of the present invention to provide an impedance spectroscopy system, not only for detecting ischemia, but also for monitoring and quantifying ischemic mucosal damage, that is of great clinical value as a therapeutic guide for patients with intestinal ischemia and/or shock.

Another primary object of the present invention is to provide a catheter, for use with an impedance spectroscopy system, that is optimized for impedance spectroscopy in hollow viscous organs.

Yet another primary object of the present invention is to provide an impedance spectroscopy system and catheter for the continuous monitoring of the level of damage of the gastric mucosa in critically ill patients.

SUMMARY OF THE INVENTION

An impedance spectroscopy system for monitoring ischemic mucosal damage in hollow viscous organs comprises a sensor catheter and an impedance spectrometer for electrically driving the catheter to obtain a complex impedance spectrum of tissue proximate the catheter. According to the present invention, the complex impedance spectrum is used to determine the extent to which the tissue is damaged, as opposed to determining if the tissue is ischemic. More specifically, as mentioned above, ischemia is a condition of inadequate blood flow and oxygen delivery to a given tissue, which may or may not result in tissue damage (i.e., ischemic tissue can be undamaged, and vice versa). Thus, detecting tissue ischemia does not result in a measurement of tissue damage, and a different process, as implemented in the present invention, must be utilized to do so.

The catheter, which is configured to be inserted into any hollow viscous organ, comprises four Ag/AgCl electrodes positioned on an end tip of the catheter. The electrodes are functionally ring-shaped, and are coaxially spaced apart a short distance from one another. The outer two ring electrodes inject current into the tissue, and the inner two electrodes measure the resulting voltage. Leads, electrically connected to the electrodes, extend along the wall of the catheter tubing or in a lumen portion of the tubing, and terminate at an interface plug suitable for connection to the impedance spectrometer. Once the catheter is in place in one of a patient's hollow viscous organs, the impedance spectrometer causes the electrodes in the tip of the catheter to inject a current into the mucosal tissue at different frequencies, allowing for the measurement of the tissue's complex impedance spectrum. The spectrum contains information of the structural and metabolic status of the tissue, and can be used to quantify the level of damage. More specifically, the spectrum can be appropriately graphically plotted against the spectrum of normal tissue, allowing for a direct visual comparison by trained personnel, and, therefore, an indication or measurement of damage. Alternatively, a standard pattern recognition system or the like may be used to automatically analyze the complex impedance spectrum and quantify the severity of the mucosal injury.

BRIEF DESCRIPTION OF THE DRAWINGS

These and other features, aspects, and advantages of the present invention will become better understood with respect to the following description, appended claims, and accompanying drawings, in which:

DETAILED DESCRIPTION OF THE INVENTION

Figure 1:
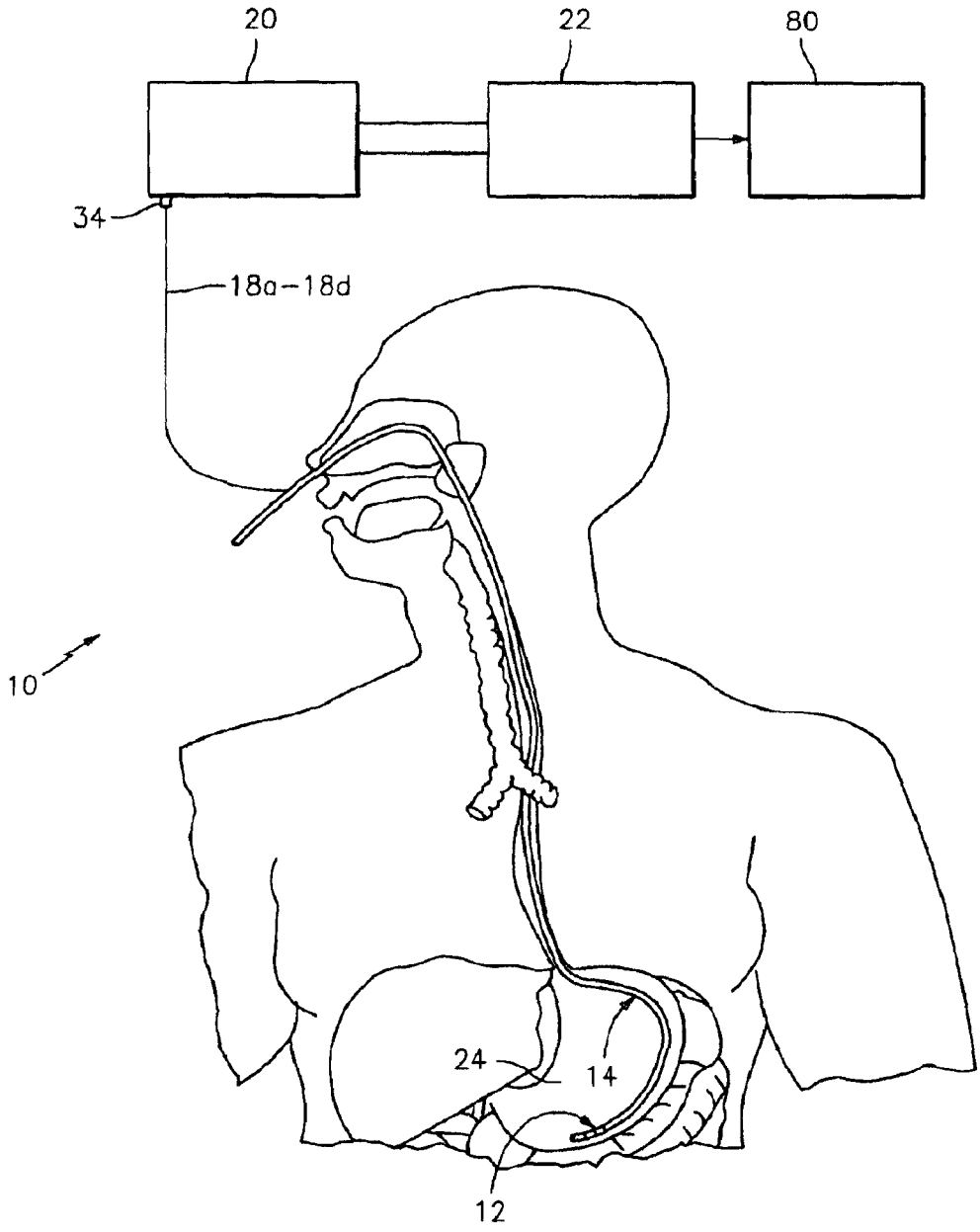
FIG. 1 is a schematic view of an impedance spectroscopy system for monitoring ischemic mucosal damage in hollow viscous organs.

Turning now to FIGS. 1-11C, preferred embodiments of an impedance spectroscopy system 10 and catheters 12a-12d for ischemic mucosal damage monitoring in hollow viscous organs, according to the present invention, will now be given. The catheters 12a-12d are generally similar, in that each one has two or four electrodes with annular side surfaces positioned at a distal end of the catheter. For example, the catheter 12a comprises a flexible tube 14 and two or four generally cylindrical electrodes 16a-16d disposed at one end thereof. The electrodes 16a-16d are electrically connected, via leads 18a-18d extending up through the tube 14, to an impedance spectrometer 20 portion of the system 10. The spectrometer 20 is used in conjunction with a signal processing device 22, such as an appropriately-programmed general purpose computer, for processing the complex impedance spectrum to detect tissue damage. To monitor mucosal damage, the catheter is placed in one of a patient's hollow viscous organs 24, and current is injected by two of the electrodes 16a, 16d at a range of frequencies. The other two electrodes 16b, 16c measure the resulting voltage spectrum, which is subsequently processed and analyzed by the spectrometer 20 and signal processing device 22.

Figure 2A:
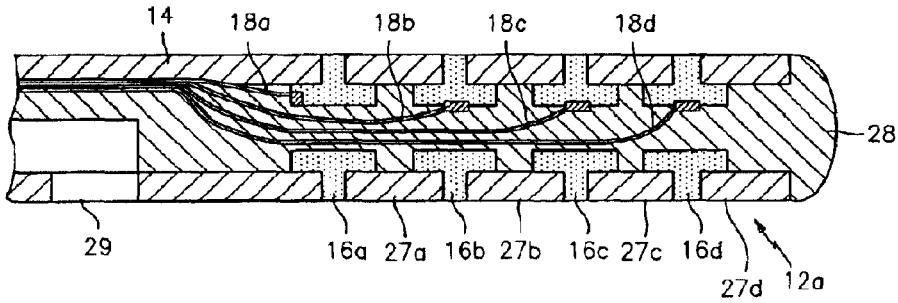
FIG. 2A is a cross-sectional elevation view of a catheter for use with the impedance spectroscopy system.
Figure 2B:
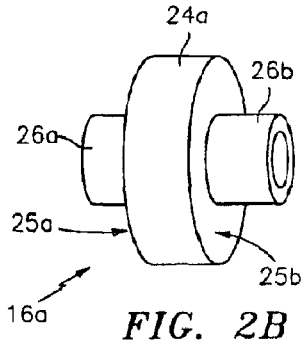
FIG. 2B is a perspective view of an electrode portion of the catheter.
Figure 2C:
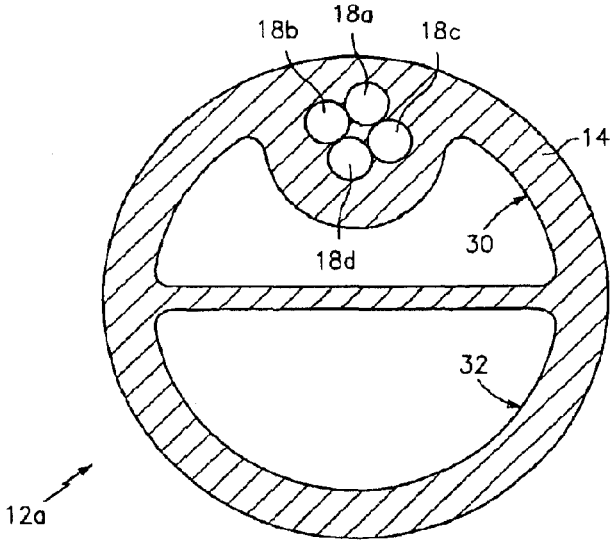
FIG. 2C is a cross-sectional plan view of an alternative upper portion of the catheter.

FIGS. 2A-2C show a first embodiment 12a of the catheter. The catheter 12a comprises the flexible plastic tube 14 that can be inserted in any hollow viscous organ (e.g., 14-16 french). At the distal end or tip of the tube 14 are located the two or four electrodes 16a-16d (i.e., the catheter can be provided with either two electrodes or four electrodes) that function as ionic-current-to-electronic-current transducers, such as Ag/AgCl electrodes. The electrodes are substantially identical. As best shown in FIG. 2B, each has a cylindrical central portion (e.g., 24a) having a first diameter and two annular side surfaces (e.g., 25a, 25b), and two cylindrical extensions (e.g., 26a, 26b) attached to the ends of the central portion and coaxial therewith. Each extension (e.g., 26a, 26b) has a second, reduced diameter, and each electrode 16a-16d has an axial through-bore.

The electrodes 16a-16d are spaced equally apart from one another along the distal tip of the catheter 12a, and are separated by spacers (short lengths of tubing) 27a-27d. As best seen in FIG. 2A, the annular side walls of the central portions 24 of the electrodes 16a-16d are the only portions thereof that are exposed to the outside of the catheter 12a. Thus, each electrode 16a-16d is ring-like in functionality, and the distal end of the catheter (with the electrodes) is generally radially symmetric. The catheter, therefore, will provide the same measurements regardless of its radial orientation in an organ.

The diameters of the central electrode portions (e.g., 24a) are about the same as the outer diameter of the tube 14. This ensures that the outer surface of the catheter 12a is relatively smooth, e.g., that it has no more than minor surface roughness or undulations. The electrodes 16a-16d are respectively electrically connected to the leads 18a-18d (via soldering, welding, or the like) in the electrodes' axial through-bores. The leads from the distal three electrodes 16b-16d extend through the axial through-bores of the other electrodes, as applicable. The electrodes 16a-16d, leads 18a-18d, and short portions of tubing are kept in place and stabilized via an epoxy or plastic fill 28.

The catheter 12a may be a stand alone sensor catheter, or it may be provided as part of a feeding/sump tube or some other type of life support tube or catheter. For example, as shown in FIG. 2A, the catheter 12a doubles as a feeding tube. More specifically, the end of the catheter 12a is provided with the electrodes 16a-16d, while the remainder of the tube 14 is left hollow to act as a feeding line 29. Additionally, the catheter tube 14 may include a second lumen for sampling and feeding, like a Levin type gastric catheter, and/or a third lumen for a vented feeding/sump tube, as in a Salem type gastric catheter. For example, as shown in FIG. 2C, the electrical leads 18a-18d extend down through a side wall portion of the tube 14 having a vent lumen 30 and a feeding/sump lumen 32.

To manufacture the catheter 12a, the leads 18a-18d are fed through the tube 14, if needed (since the leads may be provided as part of the tube 14 during the tube's manufacturing process), and through the electrode through-bores, as applicable. The leads are subsequently electrically connected to the respective electrodes. Then, the proximate electrode 16a is inserted in the end of the tube 14, one of the short lengths of tubing is affixed to the proximate electrode 16a, and so on. Adhesive may be used to hold the components together in this manner. Finally, the plastic or epoxy fill 28 is injected into the space between the tubing portions, electrodes, and partially into the tube 14, and is allowed to set. The end of the fill 28 is rounded, as shown in FIG. 2A, to ease insertion of the catheter into a patient. As will be appreciated by those of skill in the manufacturing arts, the catheter 12a can be manufactured according to a number of different methods and/or steps. For example, the catheter could be extruded from a machine.

Figure 7:
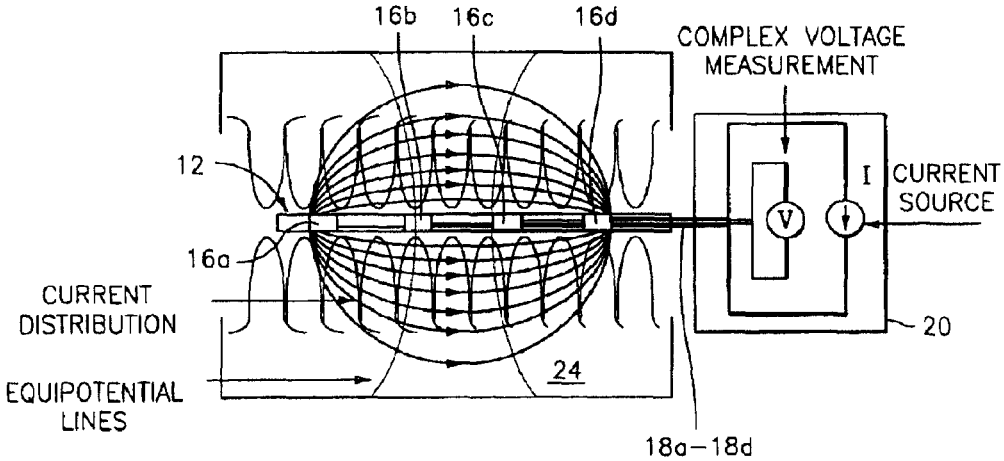
FIG. 7 is a schematic illustration of the operation of the catheter.

If the catheter 12a is provided with four electrodes, the two outer ring electrodes 16a, 16d inject a current into the tissue, and the two inner electrodes 16b, 16c measure the resulting voltage, as shown schematically in FIG. 7. In the two electrode configuration (not shown), the electrodes are used for both current source and voltage measurement. As mentioned above, the electrodes 16a-16d are respectively connected to the leads 18a-18d that provide an electrical connection to the other end of the catheter along the wall of the tubing or in the lumen. At the other, proximal end of the catheter, the leads 18a-18d end in an electrical multi-channel connector 34 that can be plugged into the impedance spectrometer 20.

Figure 3:
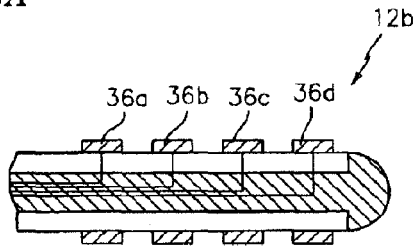
FIG. 3 is a cross-sectional elevation view of a second embodiment of the catheter.

FIG. 3 shows a second, alternative embodiment of the catheter 12b. Here, the catheter 12b has four tubular or ring-like electrodes 36a-36d simply placed over (and adhered to) the exterior surface of the tubing 14, with the leads extending from the electrodes down through the tube wall. In this case, the electrodes would have to be as thin as possible to minimize surface roughness.

Figure 4A:
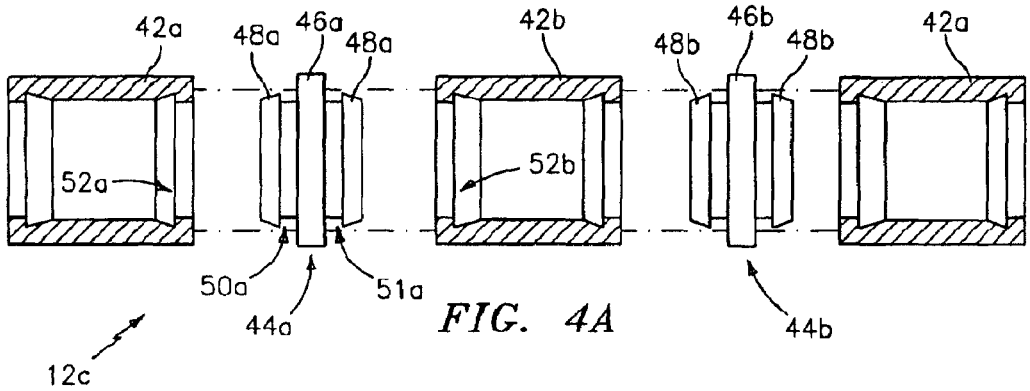
FIG. 4A is an exploded view of a third embodiment of the catheter.
Figure 4B:
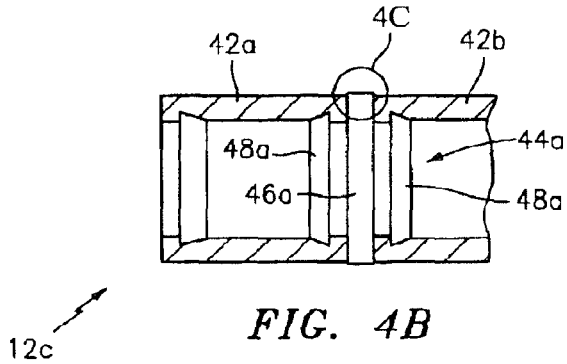
FIG. 4B is an elevation view, partly in cross-section, of a portion of the catheter shown in FIG. 4A, once assembled.
Figure 4C:
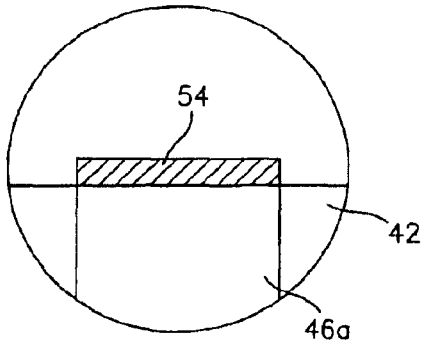
FIG. 4C is a detail view of a portion of FIG. 4A.

FIGS. 4A-4C show a third embodiment of the catheter 12c. The catheter 12c is generally similar to the catheter 12a, but has spacers (e.g., 42a, 42b, 42c), provided with annular internal sockets or spacer lips (e.g., 52a, 52b), into which flanged electrodes (e.g., 44a, 44b) lock into place. In this sample interlocking means, each flanged electrode (e.g., 44a, 44b) has a cylindrical central portion (e.g., 46a, 46b) having a first diameter and two annular side surfaces, two extensions (e.g., 48a, 48b) attached to the ends of the central portion and coaxial therewith, and an axial through-bore. The extensions (e.g., 48a, 48b) each have a second, reduced diameter, but instead of being purely cylindrical, the extensions (e.g., 48a, 48b) have annular electrode lips (e.g., 50a, 51a) that face towards the central portion 46. Additionally, the spacers (e.g., 42a-42c) are made of flexible plastic tubing (i.e., a relative non-conductor of electricity) or the like. Each spacer has two annular, inwardly-facing shoulders, in this embodiment, which form the sockets (e.g., 52a, 52b). The shoulders are spaced back a bit from the open ends of the spacers. As shown in FIG. 4B, the electrode extensions (e.g., 48a, 48b) are dimensioned to fit within the spacers (e.g., 42a, 42b) such that the electrode lips (e.g., 50a, 50b) abut the shoulders, locking the flanged electrodes (e.g., 44a, 44b) to the spacers (e.g., 42a-42c).

The catheter 12c is assembled similarly to the catheter 12a, as described above. More specifically, the leads are electrically connected to the electrodes (e.g., 44a, 44b) and are threaded through the spacers and electrodes, and the electrodes (e.g., 44a, 44b) are locked into successive spacers (e.g., 42a, 42b) to form an assembly of two or four electrodes. As should be appreciated, since the electrodes (e.g., 44a, 44b) simply snap into the spacers (e.g., 42a, 42b), assembly is much quicker. Finally, the assembly is filled with the epoxy or plastic fill 28 to further hold the assembly together and to provide a rounded tip, e.g., as shown in FIG. 2A. Also, the ends of the leads are connected to the multichannel connector 34.

To give the catheter 12c a smooth, low-friction outer surface, the diameter of the central portions (e.g., 46c) of the electrodes (e.g., 44a) may be initially slightly greater than the outer diameter of the spacers (e.g., 42a, 42b) as shown in FIG. 4C. Then, once the catheter 12c is assembled, the outer surface of the catheter is sanded, remove the portions (e.g., 54) of the electrodes that extend past the spacers.

Figure 5A:
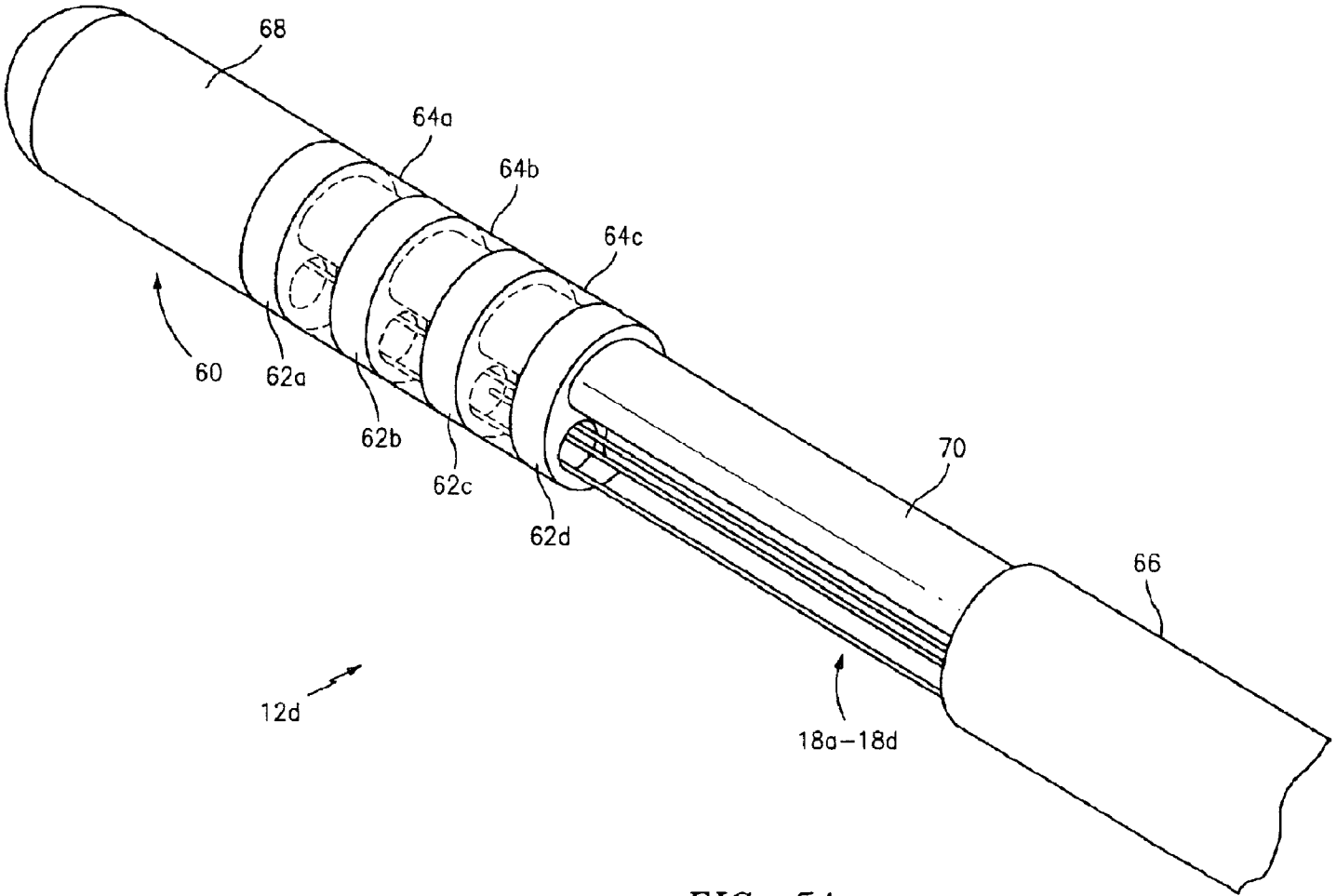
FIGS. 5A-5C are perspective views of a fourth embodiment of the catheter.
Figure 5B:
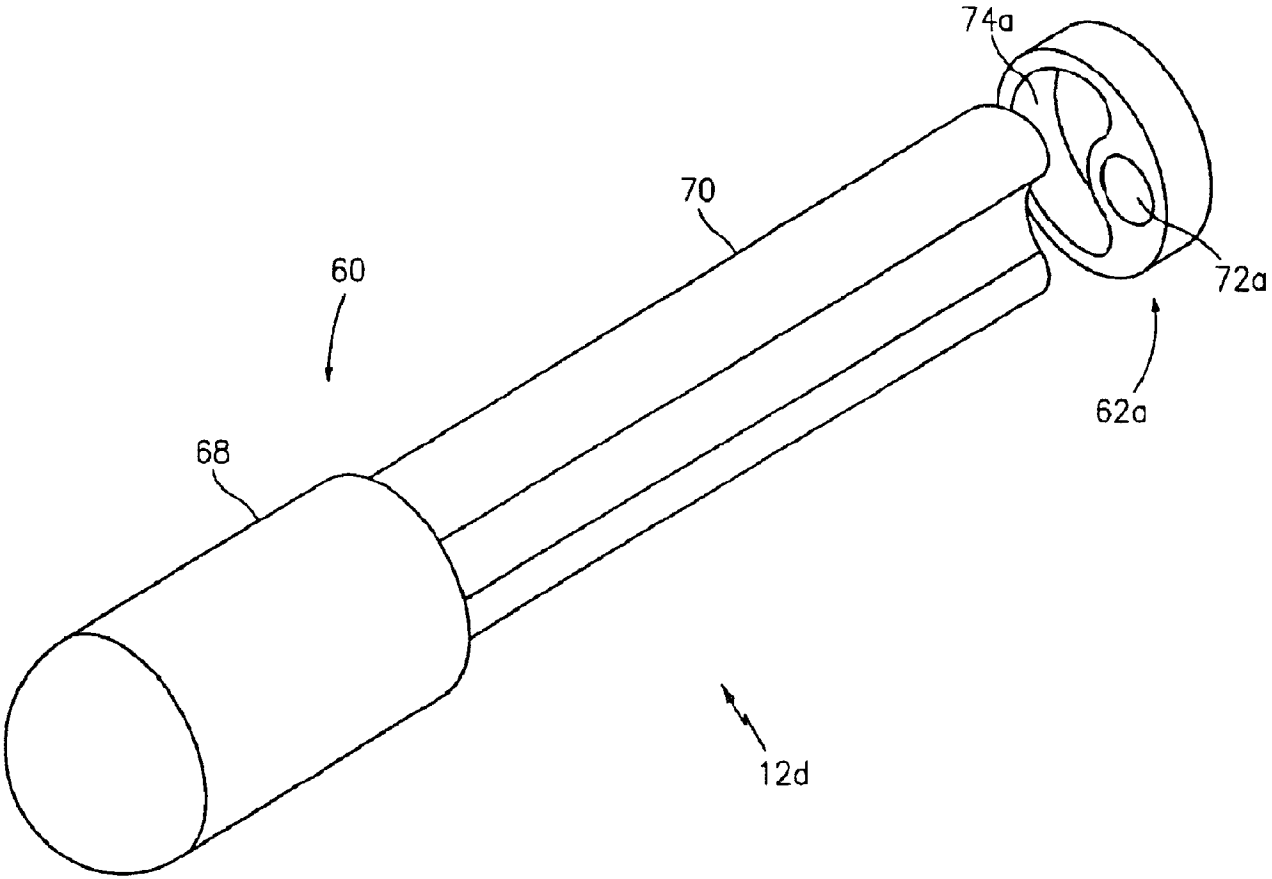
Figure 5C:
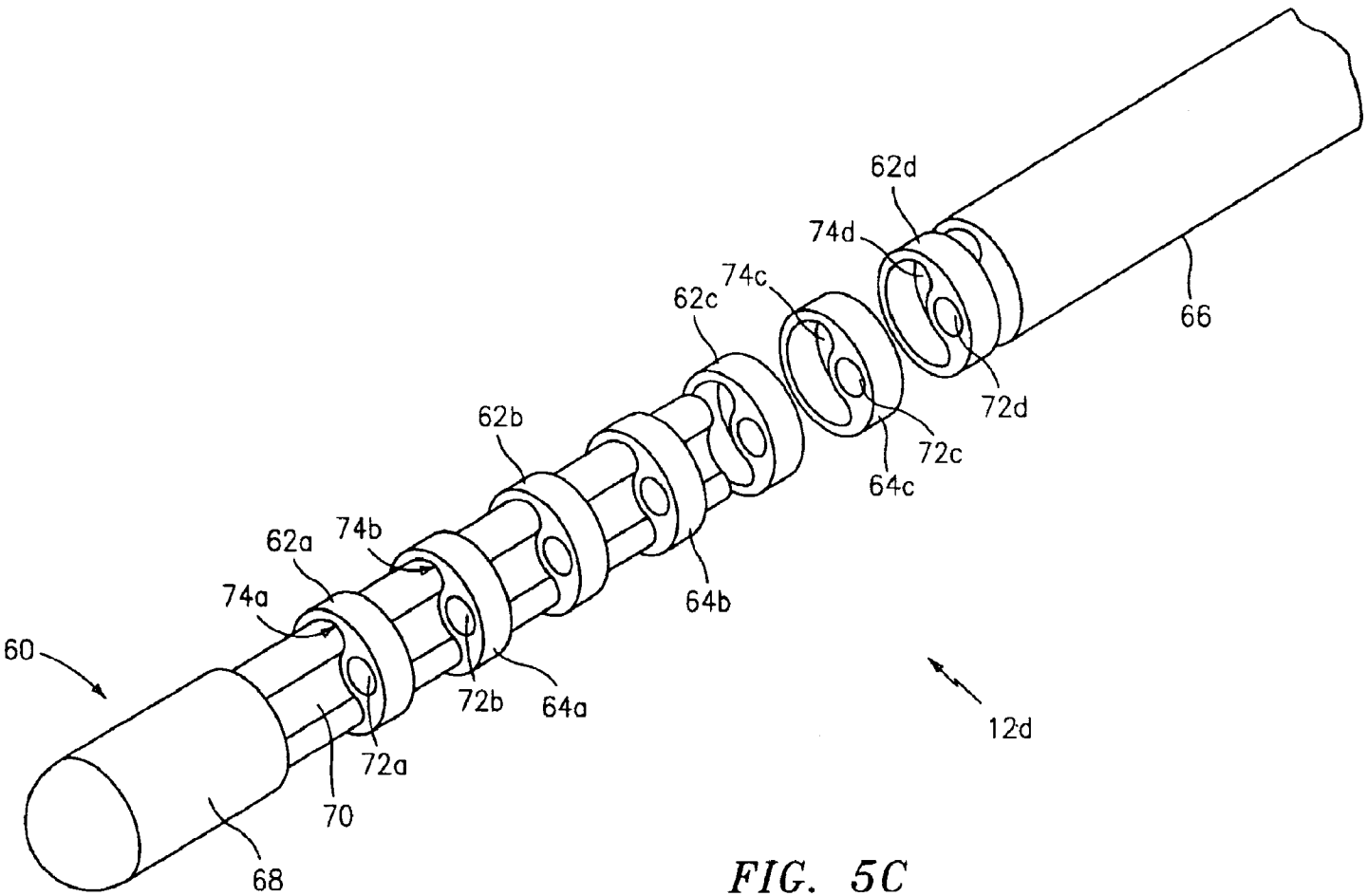
Figure 6:
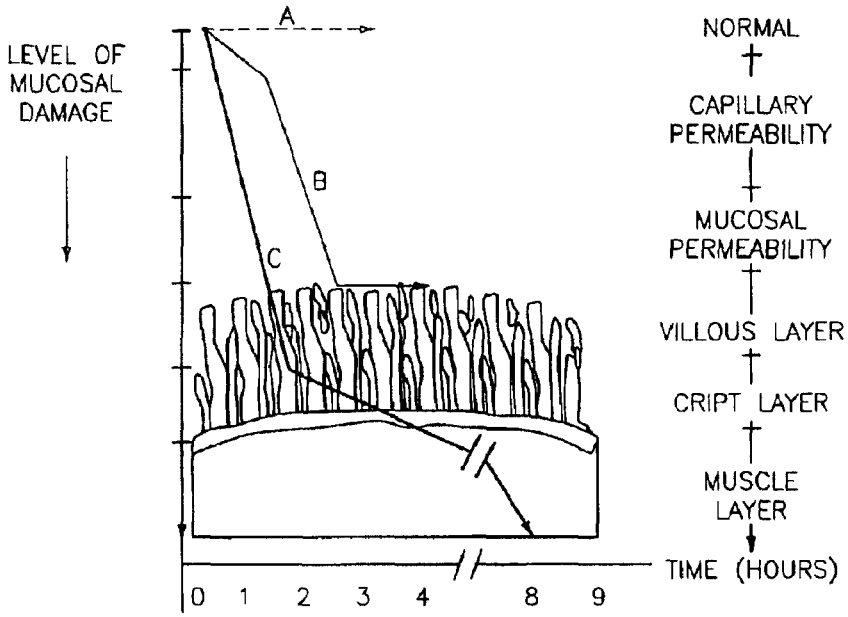
FIG. 6 is a diagrammatic graph showing mucosal structure (e.g., as lining an intestinal wall) and different courses of mucosal ischemic pathogenesis.

FIGS. 5A-5C show a fourth embodiment of the catheter 12d. The catheter 12d comprises: an injection-molded, plastic tip 60; two or four electrodes 62a-62d; one or three spacers 64a-64c (i.e., in the case of two electrodes, one spacer is needed, while three spacers are needed for a four electrode catheter); dual-lumen tubing 66 or the like; and the cables or leads 18a-18d. As best shown in FIG. 5B, the plastic tip 60 comprises a rounded fore portion 68 and a rounded, trough-like projection 70 that extends back from the fore portion 68. As indicated, the tip 60 can be injection molded, or it can be made via another suitable manufacturing process. The electrodes 62a-62d and spacers 64a-64c are generally similar in shape. Each has a small, cylindrical passageway (e.g., 72a, 72b, 72c, 72d) for the cables 18a-18d, as well as a rounded through-bore (e.g., 74a, 74b, 74c, 74d) through which the trough-like projection 70 of the tip 60 is dimensioned to fit (i.e., the rounded through-bores, e.g., 74a, 74b, 74c, 74d, and projection 70 are complementary in shape). Additionally, the outer diameters of the electrodes and spacers are the same as the outer diameter of the tip 60, which has the same outer diameter as the tubing 66. To assemble the catheter 12d, the cables 18a-18d are respectively electrically connected to the electrodes 62a-62d, and alternating electrodes 62a-62d and spacers 64a-64c are slid over the projection 70. Simultaneously, the cables 18a-18d are inserted through the passageways (e.g., 72a, 72b, 72c, 72d), as applicable. Then, the portion of the projection 70 not covered by electrodes and spacers is slid into the tubing 66, as shown in FIG. 5A. Appropriate fastening means, such as a solvent or an adhesive, are used to hold the components of the catheter 12d together.

As should be appreciated, the rounded through-bores 74 and projection 70 can be provided in any of a number of complementary shapes. For example, the projection and through-bores can be V-shaped, square, or circular. However, having a V- or trough-shaped projection, or a projection with another shape where the electrodes and spacers have to be oriented in a particular manner to be positioned over the projection, facilitates assembly and enhances structural stability.

Referring back to FIG. 1, the system 10 generally consists of three elements: any of the catheters 12a-12d; the impedance spectrometer 20; and the signal processing device 22. The impedance spectrometer 20 is an electronic instrument that includes electrical patient isolation and can measure the impedance spectrum of the mucosa in the range of 10 Hz (or thereabouts) to 10 MHz (or thereabouts). The spectrum may be obtained by a frequency sweep from a synthesizer or by a pulse, and processed by such methods as synchronous demodulation or Fast Fourier Transform, or any other similar method. The output of the spectrometer 20 is the complex impedance spectrum measured in digital form. Spectrometers and processing methods suitable for adaptation for use in the present invention are well known to those of skill in the art, for example, as shown in U.S. Pat. No. 5,807,272 to Kun et al., U.S. Pat. No. 5,633,801 to Bottman, and U.S. Pat. No. 5,454,377 to Dzwonczyk et al. The entireties of these patents are hereby incorporated by reference.

Once the complex impedance spectrum is obtained, the results are processed by the signal processing device 22. The signal processing device 22 may be an appropriately-programmed general purpose computer, or a dedicated analog and/or digital device, both of which are well known to those of ordinary skill in the art. For processing the complex impedance spectrum obtained by the spectrometer 20, the signal processing device 22 may graph or plot the spectrum for visual analysis, as discussed in further detail below. Alternatively, the signal processing device 22 may utilize a pattern recognition algorithm or system (e.g., running as software) or the like for analyzing the complex impedance spectrum itself. The pattern recognition system uses a previously trained or calibrated algorithm to classify the impedance spectrum measured and provided by the spectrometer 20. The output of this system is a numerical score (or other reference point) in an ischemic damage index scale 80 validated experimentally via MRI's, chemical analysis, biopsy samples, or the like. In other words, the signal processing device 22, implementing the pattern recognition system, analyzes the impedance spectrum to determine to what extent the impedance spectrum of the analyzed tissue deviates from that of normal tissue. The degree and character of deviation provides an actual measure of tissue damage, which translates into the ischemic damage index scale 80, as validated experimentally (e.g., heavily damaged tissue, as determined experimentally, will have a certain pattern, and slightly damaged tissue, as also determined experimentally, will have a different pattern).

More specifically, as discussed above, the impedance spectrum of the analyzed tissue is obtained by making multiple complex impedance measurements at different frequencies over the range of interest. At each frequency, an amplitude, Z, and a phase, of the tissue response are obtained. These values are then plotted as a function of frequency, or combined and plotted in the complex plane (resistance vs. reactance) in a Nyquist or a Cole-Cole plot (this latter term applies specifically to tissue impedance spectra plots), where resistance (R) and reactance (X) are defined as:

$$R=Z\cos \qquad \text{Eq. 1.}$$

$$X=Z\sin \qquad \text{Eq. 2.}$$

Analysis of these plots shows that normal tissue spectra have a characteristic shape or pattern. According to the Cole-Cole electric model of biological tissues, this shape is the arc of a circle when plotted in the complex plane. However, if tissue is damaged after an extended period of ischemia, the spectra of the damaged tissue loses this characteristic shape. In fact, when plotted in the complex plane, the spectra of the damaged tissue become sigmoid- or S-shaped, deviating significantly from the normal tissue spectra.

FIGS. 8A-11C show averaged experimental data obtained in the small intestine of a group of test subjects subjected to a period of intestinal ischemia followed by a period of reperfusion (restored blood flow), in comparison to a group of test subjects in which normal perfusion and oxygenation was maintained. The data is presented in both the frequency plots and in the complex plane. For the Nyquist plots (complex plane), the data has been normalized so that the shapes of the curves can be more easily compared, e.g., the point at the highest measurement frequency (300 KHz) has an adimensional impedance of 1 and a phase angle of 0.

Figure 8A:
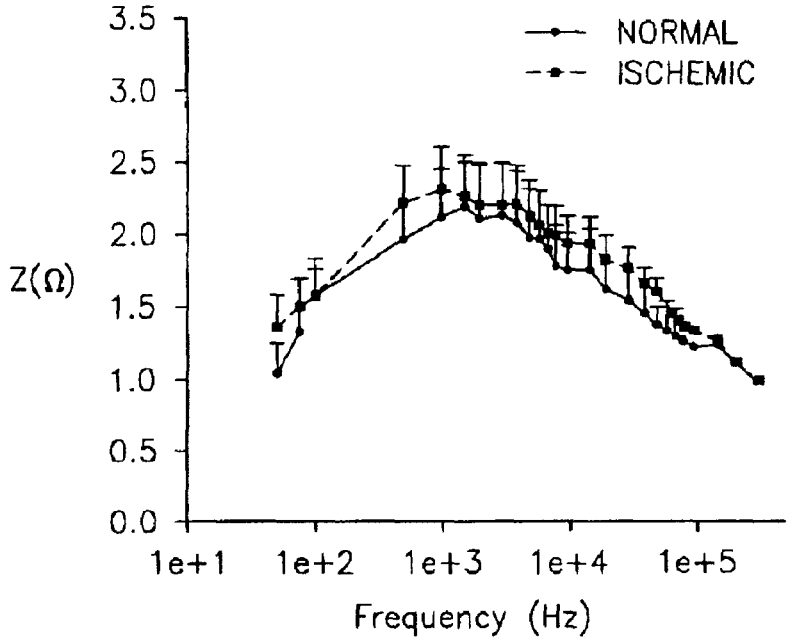
FIGS. 8A-11C are various graphs or plots illustrating how ischemic mucosal damage in hollow viscous organs is detected and/or quantified according to the present invention.
Figure 8B:
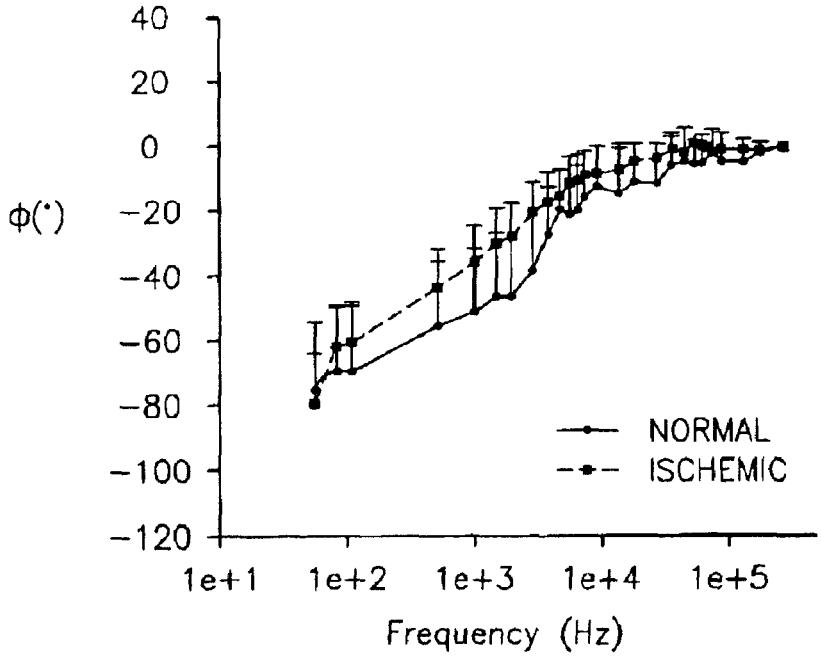
Figure 8C:
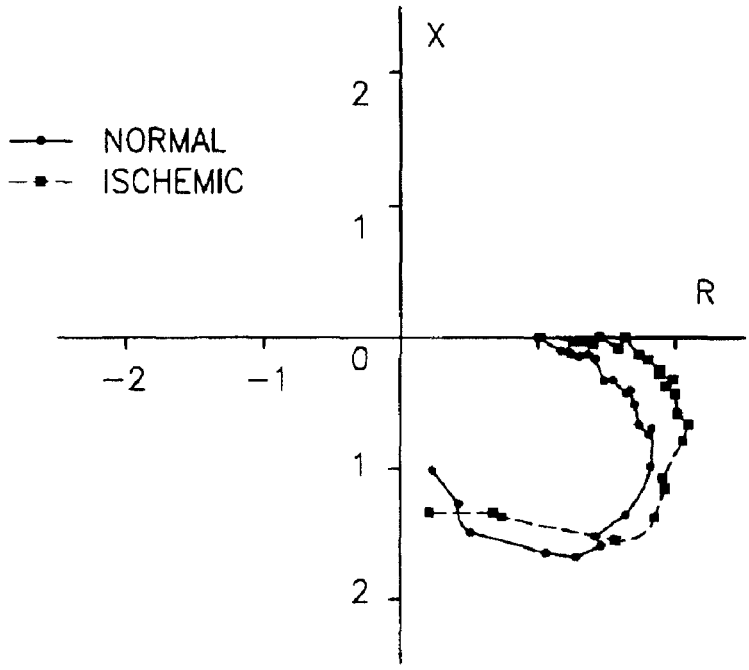

FIGS. 8A-8C show the impedance spectra of intestine with less than ten minutes of reduced blood flow, wherein the intestine is already ischemic, with associated rising acidity. In particular, FIGS. 8A and 8B show the average amplitude and phase impedance spectra, respectively, of both normal intestine and the intestine subjected to reduced blood flow, while FIG. 8C shows the normalized Nyquist plot of the normal and ischemic intestinal tissue. As can be seen, although the intestine with reduced blood flow is ischemic, the tissue is not yet damaged, and the spectra are not easily distinguishable from the spectra of the normally perfused intestines. Note that the spectra contain some noise, but resemble the circular arc predicted by the Cole-Cole model.

Figure 9A:
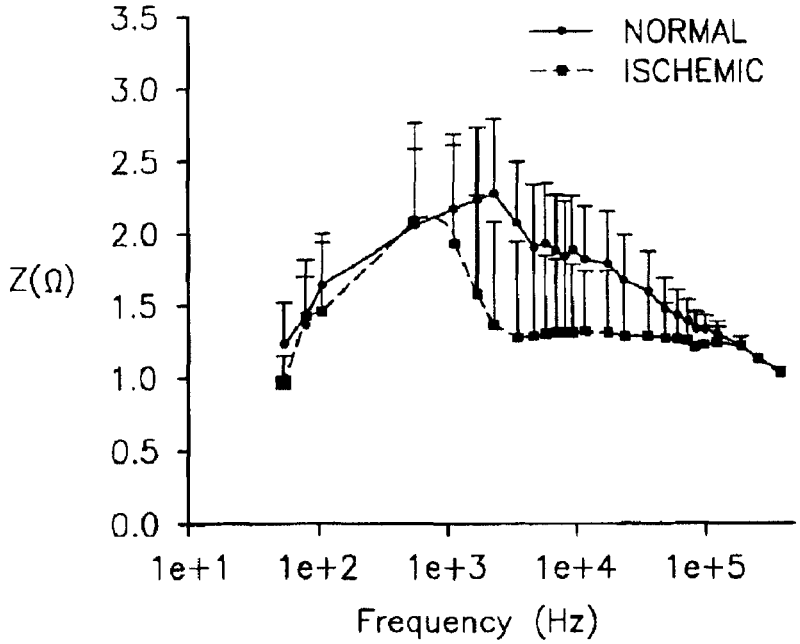
Figure 9B:
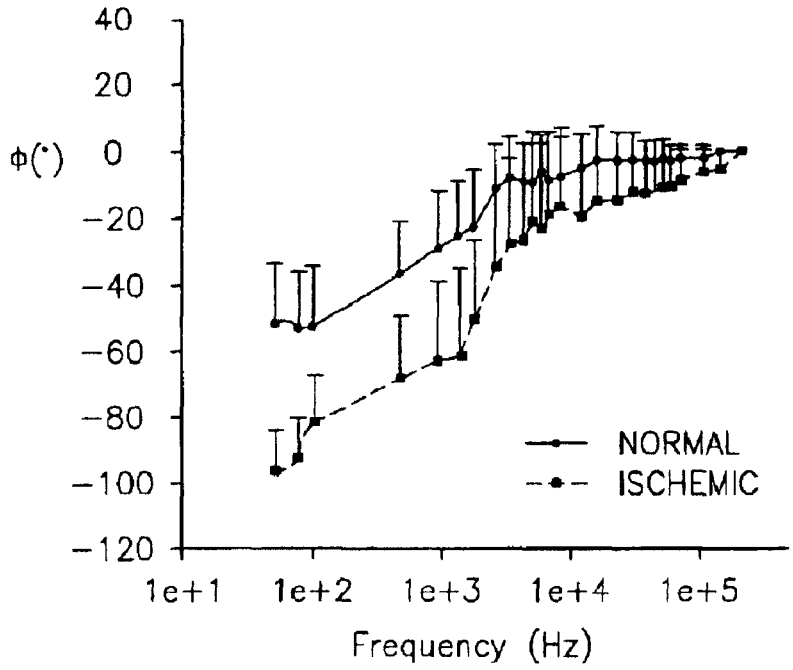
Figure 9C:
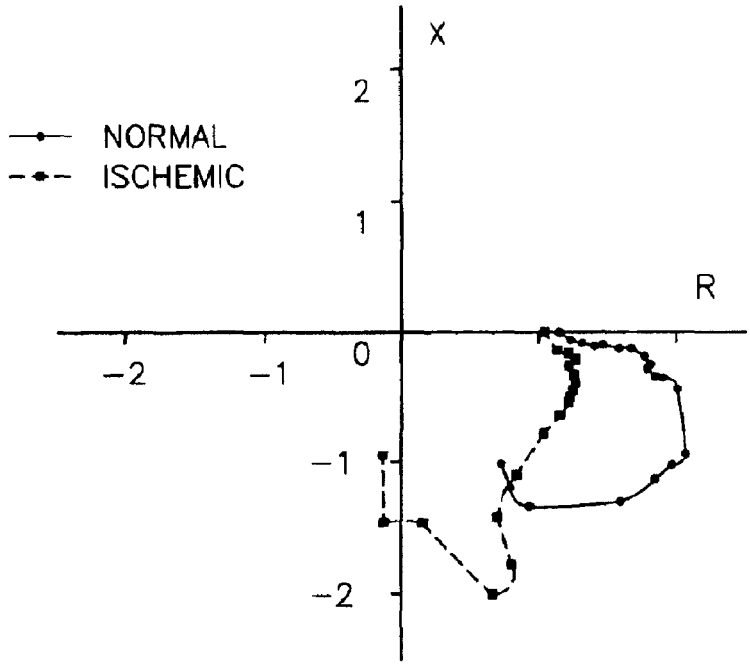

FIGS. 9A and 9B show the average amplitude and phase impedance spectra, respectively, of both normal intestine and intestine after 1.5 hours of severe ischemia, while FIG. 9C shows the normalized Nyquist plot of the normal and ischemic intestinal tissue. Here, the ischemic tissue has suffered moderate damage, and the spectra have become clearly distinguishable B the ischemic tissue spectra have lost their circular shape and have taken on a sigmoidal shape with several inflection points.

Figure 10A:
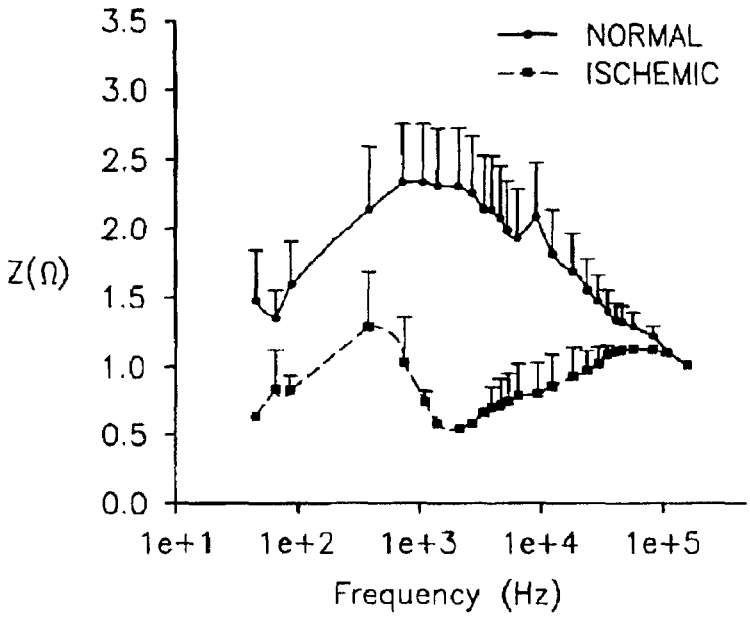
Figure 10B:
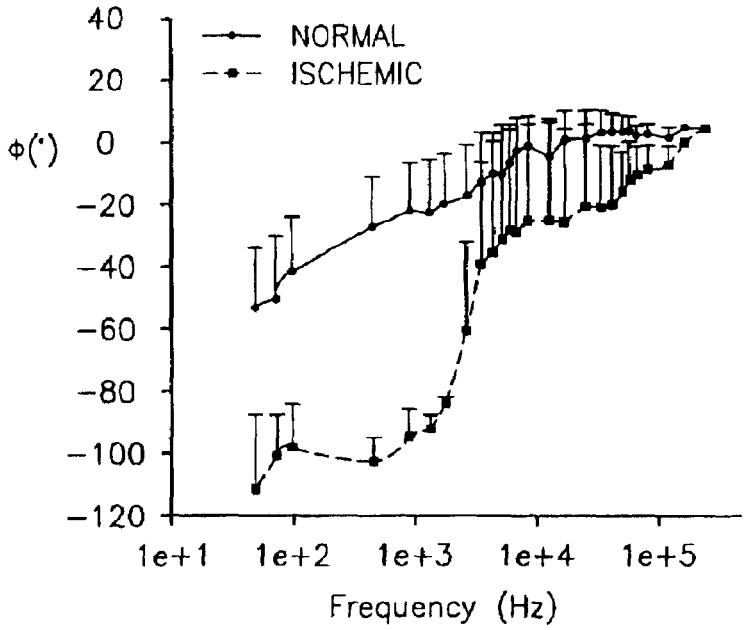
Figure 10C:
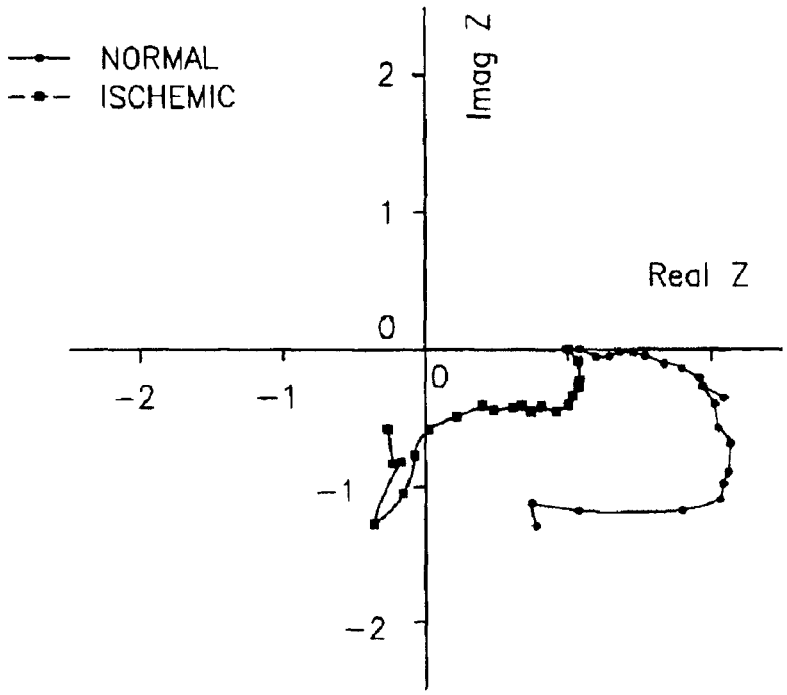

FIGS. 10A-10C show similar plots for normal intestines and intestines after two hours of severe ischemia. By now, the damage is even more severe, and the spectra have become even more distorted.

Figure 11A:
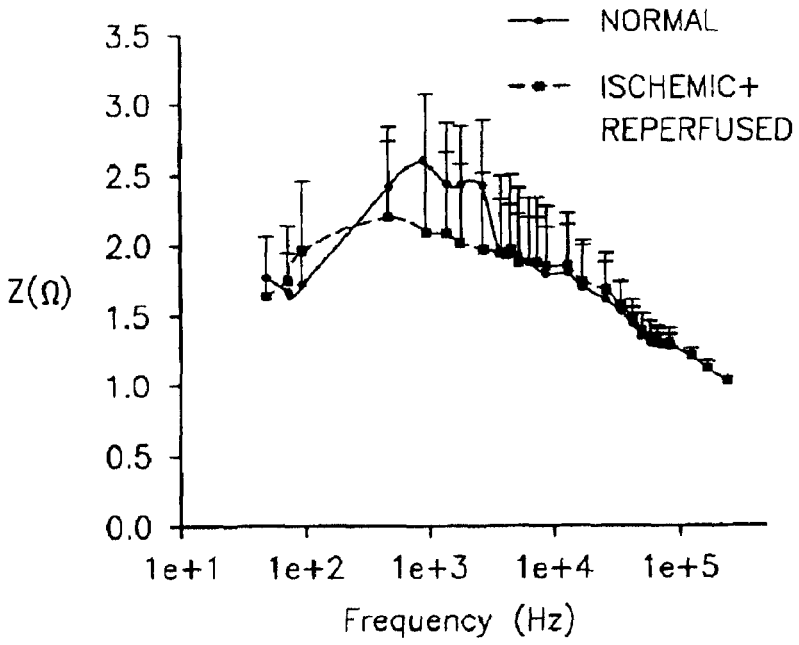
Figure 11B:
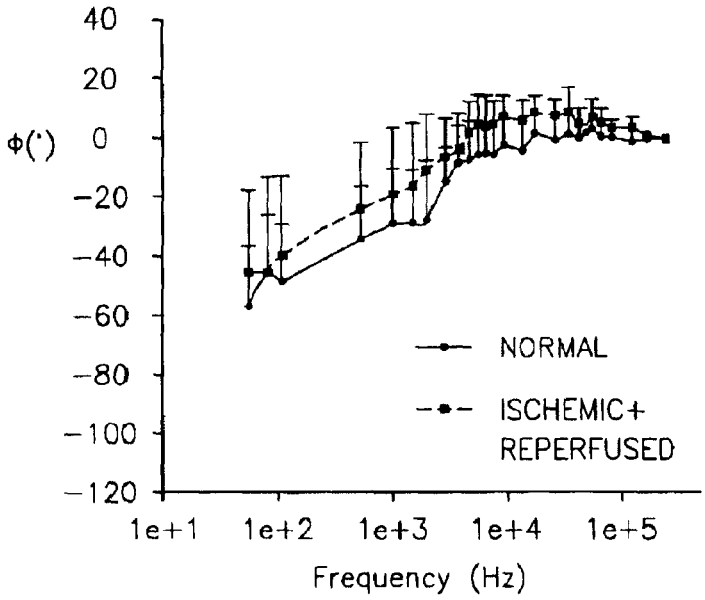
Figure 11C:
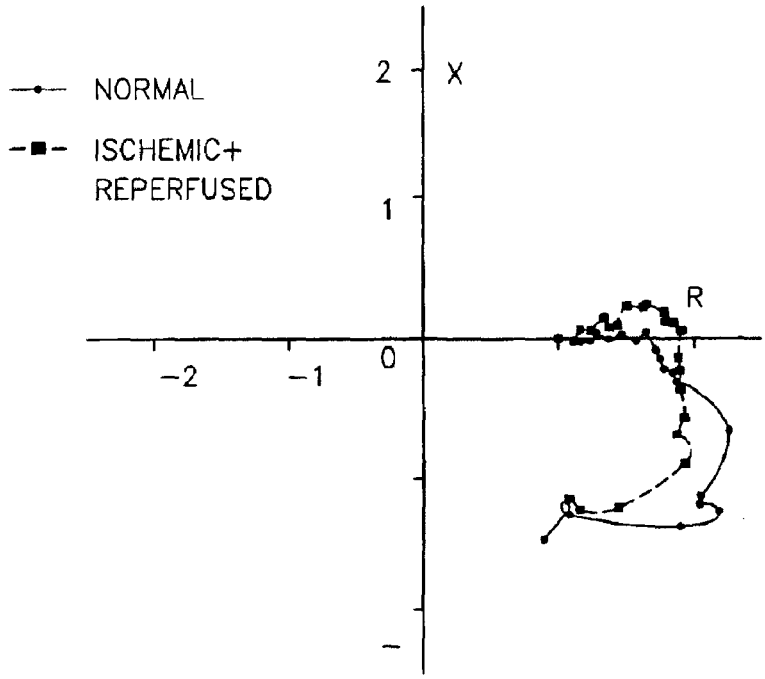

FIGS. 11A-11C show the spectra of normal intestines and intestines after an hour of ischemia followed by 1.5 hours of reperfusion. After an hour of ischemia, the tissue has suffered some damage. However, after being reperfused, most of this damage has been reversed, and the spectra of the damaged tissue have largely regained their characteristic shape, although they are still somewhat abnormal and are still moderately distinguishable from the spectra of the normal tissue.

As should be appreciated, a plot or graph of the complex impedance spectrum of potentially damaged tissue versus the spectrum of normal tissue, e.g., as shown in FIGS. 8A-11C, can be used by appropriately-trained personnel to determine the level of damage due to ischemia, by way of a visual comparison. Accordingly, the signal processing device 22 may be configured to graph or plot the spectrum for visual analysis, accordingly the general guidelines given above, on a screen or monitor, or by way of a print-out.

Alternatively, the signal processing device 22 can be configured to automatically determine tissue damage, by way of the pattern recognition system or other standard signal processing techniques, such as filtering, or smoothing and extracting inflection points by analysis of derivatives. Another alternative is the use of principal component decomposition or any other method of extracting a characteristic vector describing the shape of the spectrum. Such a characteristic vector can then be analyzed by a classifying or pattern recognition algorithm to provide a score in a predetermined tissue damage scale. Such an algorithm can use one of many standard techniques for classification and/or pattern recognition, such as Bayesian statistics, neural networks, fuzzy logic, statistical classifiers, expert systems, or any combination of these. Further detail regarding a pattern recognition system suitable for use or adaptation for use in the present invention can be found in U.S. Pat. No. 5,807,272 to Kun et al., previously incorporated by reference.

Although the catheters of the present invention have been illustrated as having Ag/AgCl electrodes, one of ordinary skill in the art will appreciate that other types of electrodes could be used instead without departing from the spirit and scope of the invention.

Although the electrodes and spacers of the fourth embodiment of the catheter have been illustrated as having separate passageways and through-bores, one of ordinary skill in the art will appreciate that the passageways and through-bores could be connected, i.e., they do not have to be separate openings, as long as there is a space for the leads.

Since certain changes may be made in the above described impedance spectroscopy system and catheter for ischemic mucosal damage monitoring in hollow viscous organs, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Having thus described the invention, what is claimed is:

[1. A catheter for use in a system for monitoring mucosal damage in hollow viscous organs, said catheter comprising:

a. a length of tubing suitable for insertion into hollow viscous organs;

b. a plurality of electrodes disposed proximate a distal end of the tubing; and c. a plurality of electrical leads respectively electrically connected to the plurality of electrodes and extending through the tubing to a proximal end thereof;

wherein:

d. the electrodes each comprise: a cylindrical central portion having an annular side wall and a diameter generally equal to an outer diameter of the tubing; first and second cylindrical extensions attached to a top and a bottom of the cylindrical central portion, respectively, and coaxial therewith, said first and second cylindrical extensions having a diameter smaller than the diameter of the cylindrical central portion; and an axial bore extending through the cylindrical central portion and first and second cylindrical extensions; and e. the electrodes are spaced apart from one another by annular spacers positioned over the cylindrical extensions and abutting the cylindrical central portions.]

[2. The catheter of claim 1 further comprising a fill extending through the spacers and axial bores of the electrodes.]

[3. A catheter for use in a system for monitoring mucosal damage in hollow viscous organs, said catheter comprising:

a. a length of tubing suitable for insertion into hollow viscous organs;

b. a plurality of electrodes disposed proximate a distal end of the tubing; and c. a plurality of electrical leads respectively electrically connected to the plurality of electrodes and extending through the tubing to a proximal end thereof;

wherein:

d. the electrodes each comprise: a cylindrical central portion having an annular side wall and a diameter generally equal to an outer diameter of the tubing; first and second cylindrical extensions attached to a top and a bottom of the cylindrical central portion, respectively, and coaxial therewith, said first and second cylindrical extensions having a diameter smaller than the diameter of the cylindrical central portion; and an axial bore extending through the cylindrical central portion and first and second cylindrical extensions; and e. the electrodes are spaced apart from one another by annular spacers positioned over the cylindrical extensions and abutting the cylindrical central portions, wherein:

i. the spacers each have two annular, inwardly-facing shoulders spaced back from the ends of the spacers; and f. the cylindrical extensions of the electrodes each have an annular lip facing towards the cylindrical central portions, wherein the cylindrical extensions are dimensioned to fit within the spacers such that the lips abut the shoulders, locking the electrodes to the spacers.]

[4. The catheter of claim 3 further comprising a fill extending through the spacers and axial bores of the electrodes.]

[5. A catheter for use in a system for monitoring mucosal damage in hollow viscous organs, said catheter comprising:

a. a tip having a rounded fore portion and a projection extending back from the fore portion;

b. a plurality of electrodes each having: an annular side surface; and a through-bore extending through the electrode and complementary in shape to the projection;

c. at least one spacer having: an annular side surface; and a through-bore extending through the spacer and complementary in shape to the projection;

d. a length of tubing suitable for insertion into hollow viscous organs; and e. a plurality of electrical leads respectively electrically connected to the plurality of electrodes; wherein:

f. the electrodes are positioned over the projection with the projection extending through the electrode through-bores, said electrodes being spaced apart from one another by the at least one spacer being positioned therebetween and over the projection with the projection extending through the spacer through-bore; and g. a rear portion of the projection lies inserted within the tubing, with the electrodes and at least one spacer being positioned between the rounded fore portion of the tip and an end of the tubing.]

[6. The catheter of claim 5 wherein the through-bores and the projection are both V-shaped.]

[7. The catheter of claim 5 wherein the through-bores and the projection both have a rounded trough shape.]

[8. The catheter of claim 5 wherein:

a. each electrode further comprises a passageway extending through the electrode;

b. the at least one spacer further comprises a passageway extending through the spacer; and c. the electrical leads extend through the electrode and spacer passageways.]

[9. The catheter of claim 5 wherein there are four electrodes and three spacers.]

[10. In a catheter for use in a system for monitoring mucosal damage in hollow viscous organs, wherein the catheter includes a length of tubing suitable for insertion into hollow viscous organs, a plurality of electrodes disposed proximate a distal end of the tubing, the improvement comprising:

a. a plurality of electrical leads respectively electrically connected to the plurality of electrodes and extending through the tubing to a proximal end thereof;

b. a plurality of annular spacers adapted in size and shape to be mounted on the catheter, and, c. means for interconnecting adjacent spaced apart pairs of the spacers with electrodes snap locking into the pairs, wherein:

i. the interconnecting electrodes each have cylindrical central portions with two annular side walls and a diameter generally equal to an outer diameter of the tubing sections: first and second cylindrical extensions attached to a top and a bottom of the cylindrical central portion, respectively, and coaxial therewith, said first and second cylindrical extensions having a diameter smaller than the diameter of the cylindrical central portion; and an axial bore extending through the cylindrical central portion and first and second cylindrical extensions; and ii. the extensions fit into through-bores of the spacers.]

*11. A catheter for use in a system for monitoring mucosal damage in hollow viscous organs, the catheter comprising:*

*a. a tip having a rounded fore portion and a projection extending back from the fore portion;*

*b. a plurality of electrodes each having: an annular side surface; and a through-bore extending through the electrode and complementary in shape to the projection;*

*c. a plurality of spacers, made of a relative non-conductor of electricity, each having: an annular side surface; and a through-bore extending through the spacer and complementary in shape to the projection;*

*d. a length of tubing suitable for insertion into hollow viscous organs;*

*e. a plurality of electrical leads respectively electrically connected to the plurality of electrodes; wherein:*

*i. the electrodes are positioned over the projection with the projection extending through the electrode through-bores, the said electrodes being spaced apart from one another by respective spacers being positioned therebetween and over the projection with the projection extending through the spacer through-bores; and*

*ii. a rear portion of the projection lies inside within the tubing, with the electrodes and at least one spacer being positioned between the rounded fore portion of the tip and an end of the tubing; and*

*f. a plurality of discrete passageways in the electrodes;*

*g. a plurality of discrete passageways in the spacers; and*

*h. the electrical leads extend separately through connecting electrode passageways and spacer passageways, whereby the leads are insulated and isolated form one another.*

*12. A catheter for use in a system for monitoring mucosal damage in hollow viscous organs, the catheter comprising:*

*a. a tip having a rounded fore portion and a projection extending back from the fore portion;*

*b. a plurality of electrodes, each having an annular side surface;*

*c. at least one spacer, made of a relative non-conductor of electricity, having an annular side surface; and a through-bore extending through the spacer, which is complementary in shape to the projection, and mounted onto the projection;*

*d. a length of tubing suitable for insertion into hollow viscous organs;*

*e. a plurality of electrical leads respectively electrically connected to the plurality of electrodes; wherein:*

*i. the electrodes are spaced apart from one another by the at least one spacer being positioned therebetween; and*

*ii. the electrodes are connected to the at least one spacer; and*

*f. discrete passageways in the electrodes;*

*g. a passageway in the at least one spacer, wherein the spacer passageway connects with one of the passageways of the electrodes; and*

*h. an electrical lead extends separately through the connecting electrode and spacer passageways, whereby the lead is insulated and isolated.*

*13. The catheter of claim 12 wherein each electrode has a through-bore.*

*14. A catheter for use in a system for monitoring mucosal damage in hollow viscous organs, the catheter comprising:*

*a. a tip having a rounded fore portion and a projection extending back from the fore portion;*

*b. a plurality of electrodes, each having an annular side surface;*

*c. at least one of the electrodes has a through-bore, which is complementary in shape to the projection, and mounted onto the projection;*

*d. at least one space, made of a relative non-conductor of electricity, having an annular side surface;*

*e. a length of tubing suitable for insertion into hollow viscous organs;*

*f. a plurality of electrical leads respectively electrically connected to the plurality of electrodes; wherein:*

*i. the electrodes are spaced apart from one another by the at least one spacer being positioned therebetween; and*

*ii. the electrodes are connected to the at least one spacer; and*

*g. discrete passageways in the electrodes;*

*h. a passageway in the at least one spacer, wherein the spacer passageway connects with one of the passageways of the electrodes; and*

*i. an electrical lead extends separately through the connecting electrode and spacer passageways, whereby the lead is insulated and isolated.*

*15. The catheter of claim 14 wherein the at least one spacer has a through-bore.*

*16. A catheter comprising:*

*a. a tip having a rounded fore portion and a projection extending back from the fore portion;*

*b. a plurality of electrodes each having: an annular side surface; and a through-bore extending through the electrode and complementary in shape to the projection;*

*c. a plurality of spacers, made of a relative non-conductor of electricity, each having: an annular side surface; and a through-bore extending through the spacer and complementary in shape to the projection;*

*d. a length of tubing suitable for insertion into hollow viscous organs;*

*e. a plurality of electrical leads respectively electrically connected to the plurality of electrodes; wherein:*

*i. the electrodes are positioned over the projection with the projection extending through the electrode through-bores, the electrodes being spaced apart from one another by respective spacers being positioned therebetween and over the projection with the projection extending through the spacer through-bores; and*

*ii. a rear portion of the projection lies inserted within the tubing, with the electrodes and at least one spacer being positioned between the rounded fore portion of the tip and an end of the tubing; and*

*f. a plurality of discrete passageways in the electrodes;*

*g. a plurality of discrete passageways in the spacers; and*

*h. the electrical leads extend separately through the connecting electrode passageways and spacer passageways, whereby the leads are insulated and isolated from one another.*

*17. A catheter comprising:*

*a. a tip having a rounded fore portion and a projection extending back from the fore portion;*

*b. a plurality of electrodes, each having an annular side surface;*

*c. at least one spacer, made of a relative non-conductor of electricity, having: an annular side surface; and a through-bore extending through the spacer, which is complementary in shape to the projection and mounted onto the projection;*

*d. a plurality of electrical leads respectively electrically connected to the plurality of electrodes; wherein:*

*i. the electrodes are spaced apart form one another by the at least one spacer being positioned therebetween; and*

*ii. the electrodes are connected to the at least one spacer; and*

*e. discrete passageways in the electrodes;*

*f. a passageway in the at least one spacer, wherein the spacer passageway connects with one of the passageways of the electrodes; and*

*g. an electrical lead extends separately through the connecting electrode and spacer passageways, whereby the lead is insulated and isolate.*

*18. A catheter comprising:*

*a. a tip having a rounded fore portion and a projection extending back from the fore portion;*

*b. a plurality of electrodes, each having an annular side surface;*

*c. at least one of the electrodes has a through-bore, which is complementary in shape to the projection, and mounted onto the projection;*

*d. at least one spacer, made of a relative non-conductor of electricity, having an annular side surface;*

*e. a plurality of electrical leads respectively electrically connected to the plurality of electrodes; wherein:*

*i. the electrodes are spaced apart from one another by the at least one spacer being positioned therebetween; and*

*ii. the electrodes are connected to the at least one spacer; and*

*f. discrete passageways in the electrodes;*

*g. a passageway in the at least one spacer, wherein the spacer passageway connects with one of the passageways of the electrodes; and*

*h. an electrical lead extends separately through the connecting electrode and spacer passageways, whereby the lead is insulated and isolated.*

*19. The catheter of claim 18 wherein the at least one spacer has a through-bore.*

*20. A catheter comprising:*

*a. a plurality of electrodes separated by spacers, made of a relative non-conductor of electricity, wherein the spacers and electrodes are interconnected;*

*b. each electrode has at least one electrode through-bore and at least one passageway extending through the electrode;*

*c. the spacers have at least one spacer though-bore aligned with at least one electrode through-bore, and have passageways which are connected to passageways in the electrodes to form discrete channels through which leads attached to respective electrodes pass; and*

*d. whereby the leads are insulated and isolated from one another.*

*21. A catheter comprising:*

*a plurality of electrodes each having an annular side surface, at least one electrode through-bore and at least one passageway extending through the electrodes;*

*at least one spacer made of a relative non-conductor of electricity, the at least one spacer connected to the electrodes and disposed to electrically isolate the electrodes from one another;*

*the at least one spacer including at least one spacer through-bore aligned with at least one electrode through-bore, and including at least one passageway connected to the at least one passageway in the electrodes; and*

*leads extending through the electrode and spacer passageways, the leads connected to corresponding electrodes.*

*22. The catheter of claim 21 further comprising a projection extending through the electrode and spacer though-bores.*

*23. The catheter of claim 22 where the electrode and spacer through-bore have a shape complementary to the shape of the projection.*

*24. The catheter of claim 22 further comprising a tip extending from the projection to a rounded fore portion.*

*25. A catheter comprising:*

*a plurality of electrodes each having an annular side surface and at least one passageway extending through the electrodes;*

*at least one spacer made of a relative non-conductor of electricity, the at least one spacer connected to the electrodes and disposed to electrically isolate the electrodes from one another;*

*the at least one spacer including at least one passageway connected to the at least one passageway in the electrodes; and*

*leads extending through the electrode and spacer passageways, the leads connected to corresponding electrodes,*

*wherein each electrode includes a cylindrical central portion having an annular side surface and first and second cylindrical extensions extending from opposite ends of the cylindrical central portion, the first and second cylindrical extensions having a diameter smaller than the diameter of the cylindrical central portion, and*

*wherein each spacer includes a through-bore to connect to the electrode by fitting the cylindrical extensions of the electrode in the spacer through-bore such that the spacer abuts to the cylindrical central portions.*

*26. The catheter of claim 25 where:*

*the spacers each include at least on annular, inwardly-facing shoulders spaced back from the ends of the spacers; and*

*the cylindrical extensions of the electrodes each include an annular lip facing the cylindrical central portions, the cylindrical extensions dimensioned to fit within the spacers such that the lips abut the shoulders to lock the electrodes to the spacers.*

*27. The catheter of claim 25 where the electrodes and spacers include aligned through-bores, the catheter further comprising:*

*a projection extending through the electrode and spacer through-bores along a length of the catheter; and*

*a length of tubing enclosing the projection through the length of the catheter and extending to cover the cylindrical extension of the first of the plurality of electrodes, the diameter of the tubing being substantially the same as tote diameter of the cylindrical central portion.*

*28. The catheter of claim 21 where the leads are insulated and isolated from one another.*

*29. A catheter comprising:*

*a plurality of electrodes each having an annular sidewall, a through-bore and at least one passageway extending through the electrodes;*

*at least one spacer made of a relative non-conductor of electricity, the at least one spacer disposed to electrically isolate the electrodes from one another, the at least one spacer including a spacer through-bore connected to the electrode through-bore, and at least one passageway connected to the at least one passageway in the electrodes;*

*a projection extending though the electrode and spacer through-bores along a length of the catheter; and*

*leads extending along the length of the catheter through the electrode and spacer passageways, the leads connected to corresponding electrodes.*

*30. The catheter of claim 29 further comprising:*

*a length of tubing enclosing the projection and the leads along the length of the catheter and extending to an end of the tubing abutting the first of the plurality of electrodes.*

*31. The catheter of claim 29 further comprising a tip extending from the projection to a rounded fore portion.*

*32. The catheter of claim 29 where the leads are insulated and isolated from one another.*

* * * * *